United States Patent [19]

Buzza et al.

[11] 4,007,105
[45] Feb. 8, 1977

[54] ELECTRODE MODULE FOR TITRATION APPARATUS

[75] Inventors: Edmund E. Buzza, Fullerton; John E. Lillig, Diamond Bar, both of Calif.

[73] Assignee: Beckman Instruments, Inc., Fullerton, Calif.

[22] Filed: July 11, 1975

[21] Appl. No.: 595,207

[52] U.S. Cl. .......................................... 204/195 T
[51] Int. Cl.$^2$ ...................................... G01N 27/44
[58] Field of Search ............... 204/195 T, 1 M, 1 B, 204/1 C, 195 C, 195 R; 23/255 E

[56] References Cited

UNITED STATES PATENTS

| | | | |
|---|---|---|---|
| 2,928,782 | 3/1960 | Leisey | 204/195 T |
| 3,551,109 | 12/1970 | Dahms | 204/1 B |
| 3,563,875 | 2/1971 | Coulson | 204/195 T |
| 3,748,247 | 7/1973 | Weisstuch | 204/195 C |
| 3,772,178 | 11/1973 | Wilson | 204/195 C |

*Primary Examiner*—G. L. Kaplan
*Attorney, Agent, or Firm*—R. J. Steinmeyer; Robert R. Meads

[57] ABSTRACT

Titration apparatus for measuring chloride electrolyte in blood samples including a pair of coulometric generator electrodes for titrating the chloride with silver ions to precipitate silver chloride and a pair of amperometric detector electrodes for detecting completion of the silver chloride precipitation. The amperometric electrodes and one of the coulometric electrodes (cathode) are contained in a unitary electrode module which is mounted separately from the remaining coulometric electrode (anode) and which is readily removable for cleaning.

10 Claims, 3 Drawing Figures

ELECTRODE MODULE FOR TITRATION APPARATUS

BACKGROUND OF THE INVENTION

1. Field of the Invention

The present invention relates generally to electrochemical titrators and, more particularly, to titration apparatus for analyzing biological or biochemical substances such as blood serum.

2. Description of the Prior Art

Titrators have long been available for analyzing chloride electrolyte in blood samples by coulometrically generating silver ions which precipitate the chloride as silver chloride and by amperometrically detecting completion of the chloride precipitation. The quantity of silver ions required to precipitate the chloride provides a measure of the amount of chloride initially present in the sample.

Such chloride titrators employ a coulometric generator comprising a pair of coulometric electrodes, typically a large silver anode and a smaller platinum cathode, and an amperometric detector comprising a pair of amperometric electrodes of silver. Both pairs of electrodes are immersed in a reagent solution such as dilute sulfuric acid into which the sample is introduced. When a voltage is applied across the coulometric electrodes, silver ions are generated at the coulometric anode and hydrogen is released at the coulometric cathode. With a small voltage applied across the amperometric electrodes, an amperometric current signal is established therebetween proportional to the quantity of uncombined silver ions present in the solution.

With the system in equilibrium, prior to introduction of a sample into the reagent solution, an initial amperometric current flows between the amperometric electrodes dependent upon the initial quantity of uncombined silver ions present in the solution. The coulometric generator is held off by the initial amperometric current signal and no silver ions are being released into the solution.

When a sample which contains chloride is introduced into the reagent solution, the chloride ions will combine with the uncombined silver ions initially present in the solution to precipitate silver chloride. The resulting decrease in uncombined silver ions results in a corresponding decrease in the amperometric current signal which is coupled to turn on the coulometric generator. Generation of silver ions then proceeds at the coulometric anode until all of the introduced chloride has been precipitated and the initial quantity of uncombined silver ions has been reestablished in the solution. At this time the amperometric current is reestablished at its initial (equilibrium) value, and the coulometric generator is turned off. The total quantity of generated silver ions is measured to provide a measure of the quantity of chloride present in the sample. This may be accomplished by integrating the current flow between the coulometric electrodes.

When protein containing solutions such as blood serum are analyzed in titrators of the type described, the amperometric electrodes and the coulometric cathode (platinum) become encrusted with protein deposits and must be frequently cleaned. When properly cleaned, these electrodes have a relatively long useful life. Cleaning of the coulometric anode (silver) is not generally required since this electrode is consumed by the generation of silver ions and therefore continuously presents a clean exposed surface to the sample.

A major difficulty in arranging the electrodes in the titrator is minimizing electrical and chemical interference between electrodes which would otherwise introduce inaccuracies in the measurement. For example, a fraction of the coulometrically generated silver ions can deposit on the coulometric cathode instead of combining with the sample chloride. Since measurement of the chloride concentration is based on the quantity of silver ions that combine with the chloride ions, if a fraction of the silver ions do not actually combine with chloride ions, then an erroneous chloride measurement is obtained.

In the past, the usual practice has been to mount the amperometric and coulometric electrodes individually in a sample receiving chamber, or at most to mount the electrodes as amperometric or coulometric electrode pairs. Mounting electrodes individually increases the complexity of the titration apparatus. Moreover, maintenance problems are encountered since the electrodes must be individually removed and cleaned.

Often, the electrodes are simply lengths of wire inserted into the top of a laboratory beaker containing the sample to be analyzed. In this form, the electrodes are relatively fragile and subject to damage during cleaning. Moreover, electrode arrangements of this nature are generally unsuited for newer automatic titration apparatus which must rapidly and reliably analyze successive samples for chloride.

SUMMARY OF THE INVENTION

Briefly and in general terms, the present invention resides in a new and improved electrode module for titration apparatus which overcomes the disadvantages of the prior electrode arrangements. The electrode module is simple, rugged, and inexpensive in construction, is easily maintained and cleaned, and is arranged to enhance electrode performance and minimize electrical and chemical interference between electrodes.

To this end, in accordance with a primary aspect of the invention, the electrodes with a long useful life but which require frequent cleaning (the amperometric anode, amperometric cathode, and the coulometric cathode) are combined into a single electrode module, and the electrode module is mounted independently from the remaining electrode (coulometric anode). The relative lengths and orientation of the electrodes within the module are selected to maximize electrode performance. The module is mounted in a manner enabling easy removal for cleaning and is ruggedly constructed to minimize damage during operation or cleaning.

Other advantages of the invention will be apparent from the following description taken in conjunction with the accompanying drawings.

DESCRIPTION OF THE PREFERRED EMBODIMENT

Figure 1:
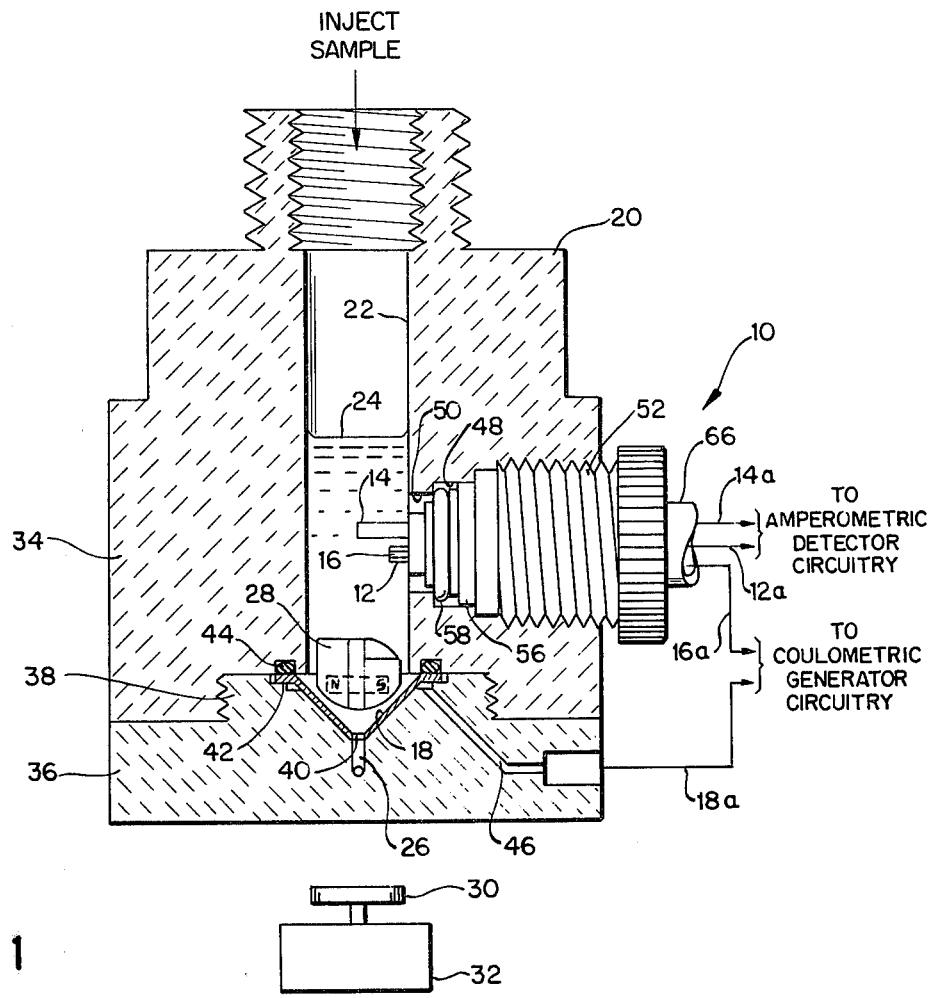
FIG. 1 is a cross-sectional view, taken in a generally vertical plane, through titration apparatus incorporating the novel electrode arrangement of the present invention.

As shown in the drawings for purposes of illustration, the present invention is embodied in titration apparatus including a novel electrode module 10 supporting an amperometric anode electrode 12, an amperometric cathode electrode 14, and a coulometric cathode electrode 16. A coulometric anode 18, independent of the electrode module 10, is operatively paired with coulometric cathode 16. The foregoing electrodes are arranged within an analysis cell 20 which receives samples of blood serum or the like for analysis. The coulometric electrodes form part of a coulometric generator for introducing ions into the sample while the amperometric electrodes form part of amperometric detector for detecting the level of uncombined ions in the sample in the manner previously described. For the generation and detection of silver ions, coulometric anode 18 and both amperometric electrodes 12 and 14 are silver, while coulometric cathode 16 is platinum.

Analysis cell 20 is formed from a block of insulating material such as polymethylmethacrylate. A cylindrical, vertically extending chamber 22, open at its upper end, is formed in the block. Samples of blood serum to be analyzed may be injected into the chamber through the upper end thereof by means of a microsampling device such as a pipette or burette in a conventional manner. Reagent 24 is supplied to and drained from the chamber through a passage 26 at the lower surface of the chamber in a conventional manner. A conventional magnetic stirring element 28 for stirring the reagent and sample is positioned in the chamber and is adapted to be rotated by a magnet 30 positioned below the cell 20 and driven by means of a motor 32.

The analysis cell 20 is preferably formed from upper and lower mating sections 34 and 36, respectively. Lower section 36 has an upstanding, threaded, central hub 38 which is threaded into upper section 34 to secure the two sections together. The lower surface of the sample chamber 22 is formed in the shape of an inverted cone in the upper surface of hub 38. Passage 26 opens into the sample chamber at the apex of the conical lower surface thereof. Passage 26, in turn, is connected to a reagent supply and to a waste receptacle through respective inlet and outlet passages (not shown) in the lower section 36 of the analysis cell.

Coulometric anode 18 is conically configured to conform to the lower surface of the sample chamber 22. In addition, anode 18 has an opening 40 at the apex thereof aligned with flow passage 26 to pass reagent into and out of the chamber. The base of the conical anode 18 has a horizontally extending, circumferential lip 42 which abuts an O-ring 44 recessed in upper section 34 of the analysis cell 20 to provide a fluid seal between the two sections of the cell.

Electrical connection is made to the anode 18 through a passage 46 in the lower section of the anaylsis cell 10. The electrical connection may comprise a platinum wire (not shown) extending through the passage 46 to the anode lip 42 and further extending directly beneath the lip about the entire circumference thereof. When the upper and lower sections 34 and 36 of the cell 20 are threaded together, the anode lip 42 is compressed by the O-ring 44 against the platinum wire to make electrical contact therewith. A conductor 18a electrically connects the platinum wire, and hence the anode 18, to coulometric generator circuitry of conventional design.

The silver coulometric anode 18 is slowly consumed during a titration operation. When a new anode is required, sections 34 and 36 of the analysis cell 20 are separated, a replacement conical anode 18 is inserted, and the sections are threaded together again.

Electrode module 10 of the invention, comprising amperometric anode 12, amperometric cathode 14, and coulometric cathode 16, is disposed in a horizontal bore 48 in the wall of the analysis cell 20 with the electrodes extending into the sample chamber 22 through a reduced diameter section 50 of horizontal bore 48. As illustrated in detail in FIG. 2, the module 10 comprises an axially extending, tubular shaped electrode case or body 54 formed from a suitable plastic such as polyvinylchloride. The three electrodes 12, 14 and 16 are securely supported by a header plug 64 seated in and sealing a left open end of the tubular body 54 while a cable 66 including electrical conductors 12a, 14a, and 16a for connection to the corresponding electrodes, extends through an open right end of the tubular body 54. An annular shoulder 56 extends from the body 54 near a left end thereof and during mounting of the module engages an externally threaded sleeve 52. As illustrated in FIG. 1, the sleeve 52 coaxially receives the body 54 and as it is advanced into the horizontal bore 48 drives the body to the left to compress an O-ring 58 between annular shoulder 62 on the header plug and a vertical face of section 50 to produce a fluid-tight seal between the chamber 22 and the horizontal bore.

Figures 2, 3:
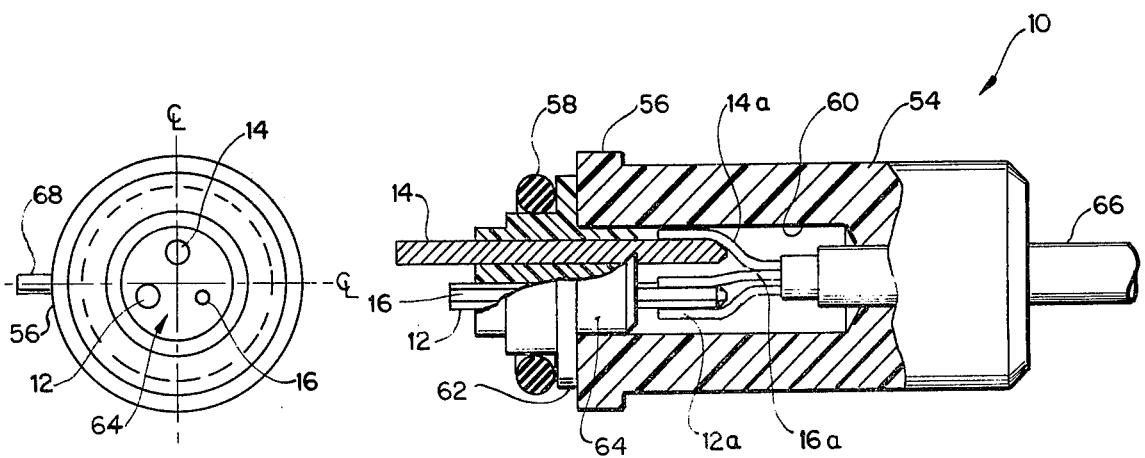
FIG. 2 is an enlarged, partial cross-sectional view of the electrode module illustrated in FIG. 1 with a portion of the module cut away to illustrate the electrodes thereof.
FIG. 3 is a left-end view of the electrode module of FIG. 2.

The three electrodes 12, 14 and 16 of the electrode module 10 are of rod-shaped configuration and are secured in a press-fit relation within three respective axially extending passages in the header plug 64. The electrodes are disposed generally parallel to one another, and, as illustrated in FIG. 3, are equally spaced around the longitudinal axis of the module 10.

Preferably, the header plug 64 is fabricated from a hydrophobic material, such as chlorotrifluoroethylene, which minimizes development of conductive films between the electrodes, resists moisture absorption, and facilitates cleaning of the electrodes and module. Further, during assembly of the module, axial bore 60 in body 54 is filled with epoxy to physically strengthen the electrical connections between the electrodes and the conductors 12a – 16a and to minimize formation of conductive paths between the electrodes resulting from moisture or the like.

As illustrated in FIG. 1, conductors 12a and 14a connect the amperometric detector electrodes 12 and 14 to amperometric detector circuitry of conventional design. Similarly, conductor 16a and the conductor 18a connect the coulometric generator electrodes 16 and 18 to coulometric generator circuitry of conventional design.

In order to orient the electrode module 10 within the horizontal bore 48 of the analysis cell 20, a metal pin 68 (FIG. 3) extends radially outward from shoulder 56 of electrode body 54. when electrode module 10 is installed in the analysis cell, the pin 68 engages a mating slot (not shown) in horizontal bore 48 to prevent the electrode module, and hence the electrodes 12, 14 and 16 thereof, from rotating within the bore.

In practice, about 1 milliliter of reagent, such as dilute sulfuric acid, is pumped into the reaction chamber 22 through passage 26, a 10 microliter blood sample is injected into the chamber, and both are mixed by magnetic stirring element 28. Chloride ions in the sample combine with silver ions initially present in the solution and precipitate as silver chloride resulting in a silver ion reduction in the solution and a reduction in the initial amperometric current signal between the amperometric detector electrodes 12 and 14. The reduced amperometric current signal enables the coulometric generator circuitry to generate silver ions at the coulometric anode 18. When all of the chloride ions in the sample have precipitated and the initial silver ion concentration has been reestablished in the solution, the initial amperometric current signal is correspondingly reestablished between the amperometric detector electrodes. This signal is coupled in a conventional manner to turn off the coulometric generator and thereby terminate the generation of silver ions. The total quantity of generated silver ions provides a measure of the initial sample chloride concentration.

The relative exposed lengths of electrodes 12, 14 and 16 and the orientation of these electrodes within the analysis cell 20 have been found to be of critical importance in optimizing operation of the titration apparatus. It is preferred that amperometric cathode 14 be positioned sufficiently remote from the coulometric anode 18 to insure that the ions generated at the anode 18 traverse as much sample as possible before reaching the vicinity of cathode 14. Similarly, coulometric cathode 16 should be sufficiently remote from coulometric anode 18 to minimize deposition of silver ions on the coulometric cathode and additionally should be positioned with respect to the amperometric cathode 14 to insure that the excess silver ions which approach the electrodes of electrode module 10 are attracted preferentially to the amperometric cathode.

In accordance with an important aspect of the invention, the exposed length of amperometric cathode 14 communicating with the sample solution is greater than that of remaining electrodes 12 and 16 of module 10. In the preferred embodiment, anode 14 is about four times longer than the remaining electrodes 12 and 16. Moreover, amperometric cathode 14 extends into the sample chamber 22 to about or beyond the center thereof. In accordance with a further aspect of the invention, cathode 14 is situated vertically above the remaining two electrodes of the module 10 as shown in FIGS. 1 and 3.

The increased length and the disposition of the amperometric cathode 14 well into the sample chamber 22 maximizes the probability that uncombined silver ions will collect at cathode 14 and thereby maximizes the sensitivity and accuracy of the amperometric detector. Moreover, since cathode 14 is situated vertically above coulometric cathode 16 (as well as coulometric anode 18) it is outside of the electrical field between the coulometric electrodes. As a result, the coulometric generator introduces minimal noise into the amperometric detector signal. Since electrodes 12 and 16 are appreciably shorter than amperometric cathode 14, they do not significantly shield or shadow cathode 14 from ions traveling from coulometric anode 18 upward to amperometric cathode 14. That is, these electrodes do not physically impede the travel of ions to the cathode 14.

It has been found that the titrator apparatus will still operate if the electrode module 10 is inverted to place amperometric cathode 14 vertically beneath the remaining electrodes 12 and 16 of the module. In this case, however, cathode 14 is situated in the electrical field between coulometric electrodes 16 and 18 and, as a result, appreciable noise is introduced into the amperometric detector output signal by the coulometric generator.

In the preferred embodiment, the silver amperometric electrodes 12 and 14 are each about 0.062 inches in diameter, while platinum coulometric cathode 16 is about 0.040 inches in diameter. As illustrated in FIG. 3, the three electrodes are equally spaced around the circumference of a circle having a diameter of approximately 0.125 inches. Amperometric cathode 14 has an exposed length of approximately 0.20 inches, and thereby has an exposed surface area of approximately 0.04 in.$^2$. Amperometric anode 12 and coulometric cathode 16 have exposed lengths of approximately 0.05 in. Thus, amperometric anode 12 has an exposed surface area of approximately 0.01 in.$^2$, and coulometric cathode 16 has an exposed surface area of approximately 0.006 in.$^2$.

It will be apparent from the above that electrode module 10 is extremely simple and rugged in construction. Further, the module is readily removed from the analysis cell 20 by unthreading sleeve 52 and simply withdrawing the module from the horizontal bore 48. Thereafter, the exposed electrode surfaces may be wiped clean and the module quickly reinserted in the analysis cell. Only one cleaning step is required, and there is minimal chance of damaging any of the electrodes during cleaning. Because of its sturdy construction, the module has a long usable life and is ideally suited for use in modern, automatic titrators for rapidly analyzing samples sequentially for prolonged periods. Moreover, while a preferred embodiment of the invention has been illustrated and described, it will be apparent that modifications may be made therein within the scope of the appended claims.

What is claimed is:

1. In titration apparatus of the type including an analysis cell having a chamber for receiving a sample to be analyzed, a coulometric generator anode and cathode electrode pair operative to generate ions combinable with a constituent of said sample, an amperometric detector anode and cathode electrode pair operative to detect the presence of uncombined ions after complete ionic combination of said constituent, the improvement comprising:

a bore communicating with said sample receiving chamber through a wall thereof;

an electrode module supporting said amperometric anode, said amperometric cathode, and said coulometric cathode in a fixed relationship, the electrodes of said electrode module being generally rod-shaped and having exposed lengths thereof disposed generally parallel to one another;

means for removably mounting said electrode module in an operative position within said bore with said exposed lengths of said electrodes communicating with said sample receiving chamber, said module being readily removable from said bore to facilitate cleaning of the electrodes thereof;

means for independently mounting said coulometric anode in operative position within said analysis cell; and wherein the exposed length of said amperometric cathode is longer than the exposed lengths of remaining ones of said electrodes to maximize collection of uncombined ions at said amperometric cathode.

2. Apparatus of claim 1 wherein said exposed length of said amperometric cathode is situated in said sample receiving chamber vertically above and said coulometric anode is situated vertically below the others of said electrodes thereby maximizing a path for ions between said coulometric anode and said amperometric cathode while minimizing physical shielding of said amperometric cathode by said others of said electrodes to ions generated at said coulometric anode.

3. Apparatus of claim 2 wherein the exposed lengths of said electrodes of said module are equally spaced about a longitudinal axis thereof.

4. Apparatus of claim 2 wherein said exposed length of said amperometric cathode extends to about a center of said sample receiving chamber or beyond.

5. Apparatus of claim 4 wherein said exposed length of said amperometric cathode is approximately four times the exposed length of said coulometric cathode.

6. Apparatus of claim 5 wherein the exposed lengths of said coulometric cathode and said amperometric anode are approximately the same.

7. Electrochemical titration apparatus operative by coulometric ion generation and amperometric ion detection and including an analysis cell having a chamber for receiving a sample to be analyzed, a coulometric generator anode and cathode electrode pair operative to generate ions combinable with a constituent of said sample, an amperometric detector anode and cathode electrode pair operative to detect the presence of uncombined ions after complete ionic combination of said constituent, means supporting said amperometric cathode electrode, said amperometric anode electrode, and said coulometric cathode electrode proximate one another in a fixed relationship, the supported electrodes having exposed lengths communicating with said sample receiving chamber and hence adapted to communicate with the sample to be analyzed, and the exposed length of said amperometric cathode exceeding that of the remaining supported electrodes to maximize collection of uncombined ions at said amperometric cathode.

8. Apparatus of claim 7 wherein the exposed lengths of said amperometric cathode, said amperometric anode, and said coulometric cathode are generally rod-shaped, wherein the exposed lengths of said amperometric cathode and said amperometric anode have substantially the same diameter, said amperometric anode and said coulometric cathode have substantially the same exposed length, and the diameter of the exposed length of said coulometric cathode is less than that of said amperometric cathode and said amperometric anode.

9. Apparatus of claim 8 wherein the exposed length of said amperometric cathode is about four times greater than that of the remaining supported electrodes.

10. Apparatus of claim 7 wherein said coulometric anode is situated in said sample receiving chamber displaced from said supported electrodes with said amperometric cathode being the most remote of said supported electrodes from said coulometric anode thereby maximizing a path for ions between said coulometric anode and said amperometric cathode while minimizing physical shielding of said amperometric cathode by others of said supported electrodes to ions generated at said coulometric anode.

* * * * *